(12) United States Patent
Urich

(10) Patent No.: US 8,475,402 B2
(45) Date of Patent: Jul. 2, 2013

(54) ASPIRATION SYSTEM FOR MEDICAL DEVICES

(75) Inventor: Alex Urich, Rancho Santa Margarita, CA (US)

(73) Assignee: Data, LLC, Irvine, CA (US)

( * ) Notice: Subject to any disclaimer, the term of this patent is extended or adjusted under 35 U.S.C. 154(b) by 2295 days.

(21) Appl. No.: 11/196,044

(22) Filed: Aug. 2, 2005

(65) Prior Publication Data

US 2006/0058729 A1  Mar. 16, 2006

Related U.S. Application Data

(63) Continuation-in-part of application No. 11/186,029, filed on Jul. 20, 2005, now abandoned.

(60) Provisional application No. 60/610,846, filed on Sep. 16, 2004.

(51) Int. Cl.
*A61B 17/20* (2006.01)
*A61M 5/00* (2006.01)

(52) U.S. Cl.
USPC .............................................. 604/22; 604/196

(58) Field of Classification Search
USPC ............................................ 604/22, 126, 190
See application file for complete search history.

(56) References Cited

U.S. PATENT DOCUMENTS

| | | | |
|---|---|---|---|
| 4,038,194 A * | 7/1977 | Luceyk et al. | 210/436 |
| 5,173,196 A | 12/1992 | Macrae | |
| 5,308,342 A * | 5/1994 | Sepetka et al. | 604/525 |
| 5,318,560 A * | 6/1994 | Blount et al. | 606/4 |
| 5,476,448 A | 12/1995 | Urich et al. | |
| 5,807,353 A | 9/1998 | Schmitz | |
| 5,954,692 A | 9/1999 | Smith et al. | |
| 6,273,878 B1 * | 8/2001 | Muni | 604/265 |
| 6,425,883 B1 | 7/2002 | Urich et al. | |
| 6,436,077 B1 * | 8/2002 | Davey et al. | 604/247 |
| 6,478,781 B1 | 11/2002 | Urich et al. | |
| 6,585,708 B1 | 7/2003 | Maaskamp | |
| 6,599,271 B1 | 7/2003 | Easley | |
| 6,780,166 B2 | 8/2004 | Kanda et al. | |
| 6,811,713 B2 * | 11/2004 | Arnaud | 210/788 |
| 7,083,591 B2 | 8/2006 | Cionni | |
| 2002/0022810 A1 | 2/2002 | Urich | |
| 2002/0124346 A1 | 9/2002 | Steiner et al. | |
| 2002/0128560 A1 | 9/2002 | Urich | |
| 2004/0069714 A1 | 4/2004 | Ferguson | |
| 2005/0159758 A1 | 7/2005 | Laks | |
| 2006/0058728 A1 | 3/2006 | Urich | |

(Continued)

*Primary Examiner* — Nicholas Lucchesi
*Assistant Examiner* — Rebecca E Eisenberg
(74) *Attorney, Agent, or Firm* — Joshua C. Harrison, Esq.; Barcelo, Harrison & Walker, LLP

(57) ABSTRACT

An aspiration tube has a relatively high fluidic resistance. The tube is coupled to a medical device and a pump of an aspiration system. The tube can be designed to create a pressure drop that at least equals the maximum vacuum pressure of the pump. The fluidic resistance can be accomplished with a tube having an inner diameter less than 0.05 inches. The aspiration tube and an irrigation tube may be coupled to an anterior chamber of a cornea during a phaco procedure. The aspiration tube is sized so that even if a maximum pressure occurs, the resultant aspiration flowrate will be such that the cornea will not be damaged when an occlusion is cleared from the tube. An in-line filter may also be attached to the aspiration tube to filter out particles in the system.

12 Claims, 2 Drawing Sheets

U.S. PATENT DOCUMENTS

2006/0058729 A1 3/2006 Urich
2006/0173426 A1 8/2006 Urich et al.
2007/0055209 A1 3/2007 Patel et al.
2007/0129694 A1 6/2007 Opie et al.

* cited by examiner

ASPIRATION SYSTEM FOR MEDICAL DEVICES

CROSS-REFERENCE TO RELATED APPLICATION

The present application is a Continuation-in-part of U.S. application Ser. No. 11/186,029 filed on Jul. 20, 2005, now abandoned, and claims priority to Provisional Application No. 60/610,846, filed on Sep. 16, 2004, now expired.

BACKGROUND OF THE INVENTION

1. Field of the Invention

The present application relates to an aspiration tube for a medical aspiration system.

2. Prior Art

The lens of a human eye may develop a cataracteous condition which affects a patients vision. Cataracteous lenses are sometimes removed and replaced in a procedure commonly referred to as phacoemulsification. Phaco procedures are typically performed with an ultrasonically driven handpiece which is used to break the lens. The broken lens is removed through an aspiration line that is coupled to the handpiece.

The handpiece has a tip which is inserted through an incision in the cornea. The handpiece typically contains a number of ultrasonic transducers that convert electrical power into a mechanical oscillating movement of the tip. The distal end of the tip has an opening that is in fluid communication with the aspiration line. The distal end of the tip also has a sleeve which has an opening in fluid communication with an irrigation line. The irrigation line is typically connected to a bottle that can provide irrigation fluid to the surgical site.

The oscillating movement of the tip breaks the lens into small pieces. The lens pieces and irrigation fluid are drawn into the aspiration line through the opening of the tip. When performing a phaco procedure it is essential to maintain a positive pressure within the anterior chamber of the eye. A negative pressure may cause the cornea to collapse. To maintain a positive chamber pressure the system is configured to provide a flow rate through the irrigation tube that is greater than the flow rate through the aspiration tube.

It has been found that the aspiration tube may become occluded during a procedure. The occlusion will increase the vacuum pressure within the aspiration line. When the occlusion is cleared the anterior chamber may be instantaneous exposed to a high vacuum pressure. The vacuum pressure may cause the cornea to collapse.

U.S. Pat. No. 6,478,781 issued to Urich et al. discloses a coiled tube that can be used to minimize pressure surges in an aspiration system. The tube has a length of at least 8 feet and a number of coils that create a fluidic resistance which minimizes vacuum surges. The recited inner diameter of the tube ranged from 0.06 to 0.1 inches, which is industry standard. Although effective, the coiled approach can only account for a limited pressure drop.

U.S. Pat. No. 6,599,271 issued to Easley and assigned to Syntec, Inc. discloses an aspiration system that has a flow restrictor and an in-line filter. Although flow restrictors can minimize vacuum surges, restrictors can create turbulent flow within the aspiration tube. Such turbulent flow can create air bubbles in the tube. When an occlusion occurs the air bubbles can collect and expand the tube. This may lead to an undesirable vacuum surge within the system.

It would be desirable to provide an aspiration system that minimizes the effects of a cleared occlusion within an aspiration tube of the system without having to use a flow restrictor, or coiled tubing.

BRIEF SUMMARY OF THE INVENTION

An aspiration tube for an aspiration system of a medical system is disclosed and claimed. The aspiration tube has an inner diameter less than 0.05 inches.

DETAILED DESCRIPTION

Disclosed is an aspiration tube that has a relatively high fluidic resistance. The tube is coupled to a medical device and a pump of an aspiration system. The tube can be designed to create a pressure drop that at least equals the maximum vacuum pressure of the pump. The fluidic resistance can be accomplished with a tube having an inner diameter less than 0.05 inches. The aspiration tube and an irrigation tube may be coupled to an anterior chamber of a cornea during a phaco procedure. The high resistance of the aspiration tube minimizes the instantaneous change of flow rate out of the cornea in the event an occlusion is cleared from the tube. The aspiration tube is sized so that even if a maximum pressure occurs, the resultant aspiration flow rate will be such that the cornea will not be damaged when an occlusion is cleared from the tube. An in-line filter may also be attached to the aspiration tube to filter out particles in the system.

Figure 1:
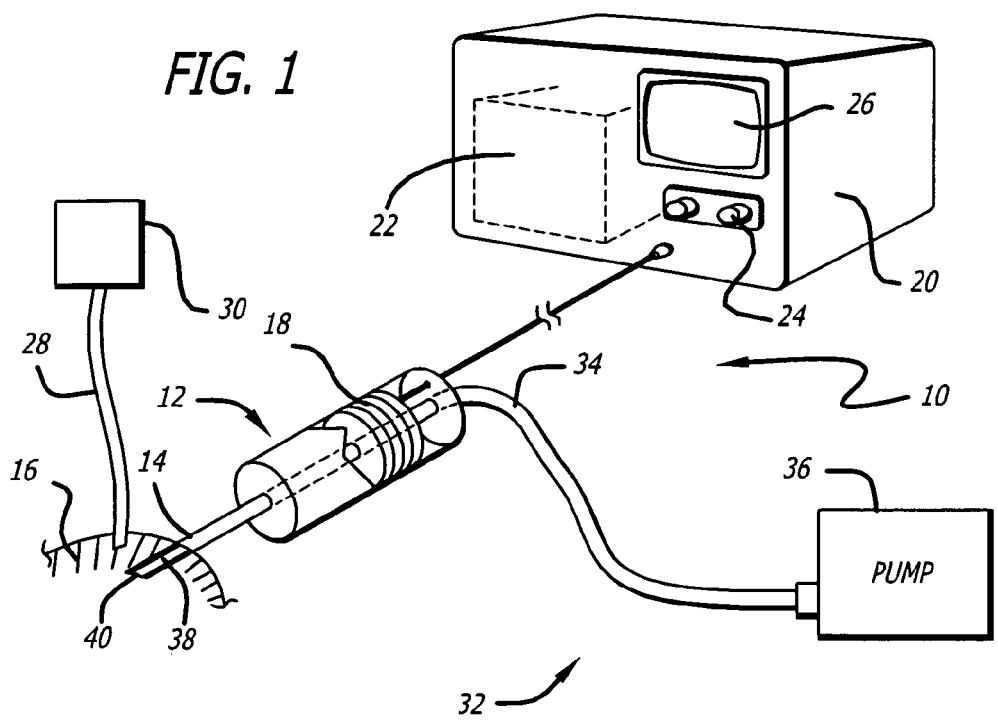
FIG. 1 is an illustration of a medical system with an aspiration system.

Referring to the drawings more particularly by reference numbers, FIG. 1 shows an embodiment of a medical system 10. The system 10 may include an ultrasonically driven handpiece which has a tip 14 that can be inserted into a cornea 16. The tip 14 may also be referred to as a cutting element. The handpiece 12 may include one or more ultrasonic transducers 18 that convert electrical power into mechanical movement of the tip 14. The handpiece 12 is typically held by a surgeon who performs a surgical procedure with the system 10. By way of example, the system 10 can be used to perform a phacoemulsification procedure to break and aspirate a lens of the cornea 16.

The handpiece 12 may be connected to a console 20 of the system 10. The console 20 may contain a control circuit 22 that provides a driving signal to the transducers 18. The console 20 may have input knobs or buttons 24 that allow the surgeon to vary different parameters of the system 10. The console 20 may also have a readout display 26 that provides an indication of the power level, etc. of the system 10.

The system 10 may include an irrigation tube 28 that is connected to an irrigation bottle 30. The irrigation tube 28 can be inserted into the cornea 16. The irrigation bottle 30 may contain an irrigation fluid that flows into the cornea 16 through the irrigation tube 28.

The medical system 10 may further have an aspiration system 32 that aspirates the irrigation fluid and broken lens out of the cornea 16. The aspiration system 32 may include an aspiration tube 34 that is connected to the handpiece 12 and a vacuum pump 36. The aspiration tube 34 is in fluid communication with an inner channel 38 and an opening 40 of the tip 14. The vacuum pump 36 creates a negative pressure within the aspiration tube 34 to induce a flow of irrigation fluid and emulsified tissue out of the cornea 16. The pump 36 is configured so that the flow rate through the irrigation tube 28 is slightly greater than the flow rate through the aspiration tube 34.

The aspiration tube 34 has a relatively large fluidic resistance to create a large fluid inertia in the aspiration system 32. The large inertia minimizes instantaneous changes in the flow rate of the irrigation fluid flowing through the aspiration tube 34. Thus if an occlusion is cleared within the aspiration tube 34, the large fluidic resistance will restrict the variation in aspiration fluid flow and minimize the probability of a cornea collapse event.

The aspiration tube 34 has a diameter less than 0.05 inches and a length of at least 3 feet. By way of example, the tube 34 may have a diameter of 0.04 or 0.035 inches, and a length of 6 feet. It is desirable to create a fluidic resistance that causes a pressure drop approximately equal to the maximum vacuum pressure of the pump. This will minimize the change in flow rate within the aspiration system in the event a maximum pressure occurs because of an occlusion within the tube 34. The tube inner diameter may have a lower limit of 0.01 inches to insure flow of emulsified lens tissue.

By way of example, most ophthalmic systems are constructed to allow for a maximum aspiration free flow rate of 50 or 60 cc/min. The flow rate is less than the infusion rate, typically 60 to 100 cc/min, to insure a positive pressure in the cornea. A flow rate greater than these values may cause a negative pressure in the cornea. Therefore it is desirable to have an aspiration system that does not allow for a flow rate greater than 50 or 60 cc/min. Many conventional vacuum pumps can create a maximum pressure of 500 mmHg. Thus the aspiration tube 34 should have a fluidic resistance that does not allow for a flow rate greater than 50 cc/min at a vacuum pressure of 500 mmHg. By way of example, the tube 34 may create a pressure drop of at least 150 mmHg.

Table I provides results of a test using 3 different tube samples. All 3 samples had a length of 6 feet. One of the samples was a conventional prior art aspiration tube having an inner diameter of 0.06 inches. The other tube samples had inner diameters of 0.04 and 0.035 inches, respectively. A vacuum pressure of 500 mmHg was applied for each sample. As shown by Table I, the 0.06 inch tube allowed a flow rate of 230 cc/min, which far exceeds the maximum value of 50-60 cc/min. The 0.04 and 0.35 inch tubes allowed flow rates below the maximum flow rate.

Table I

TABLE I

| Tubing Diameter (inch) | Tubing Length (feet) | Flow Limit (cc/min) | Pressure Drop (mmHg) |
| --- | --- | --- | --- |
| 0.060 | 6.0 | 230 | 500 |
| 0.040 | 6.0 | 45 | 500 |
| 0.035 | 6.0 | 27 | 500 |

As shown by the results in Table I, the aspiration tubes below 0.05 inches created enough fluidic resistance to prevent excessive fluid flow even at a vacuum pressure of 500 mmHG.

Figure 2:
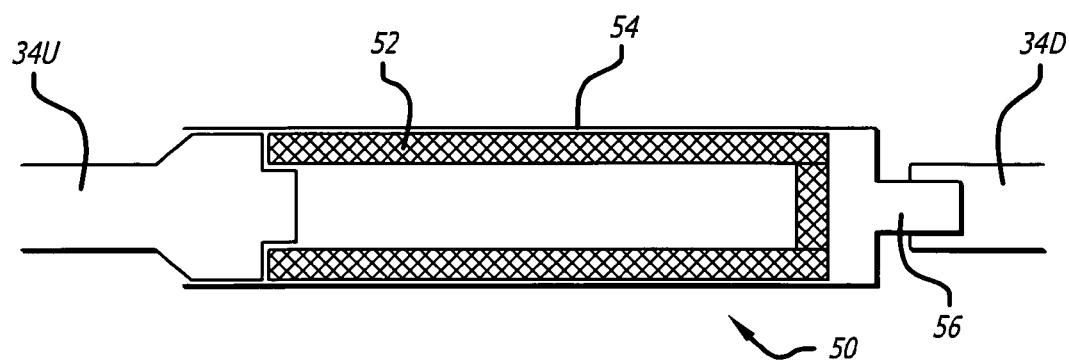
FIG. 2 is an illustration of an in-line filter of the aspiration system.
Figure 3:
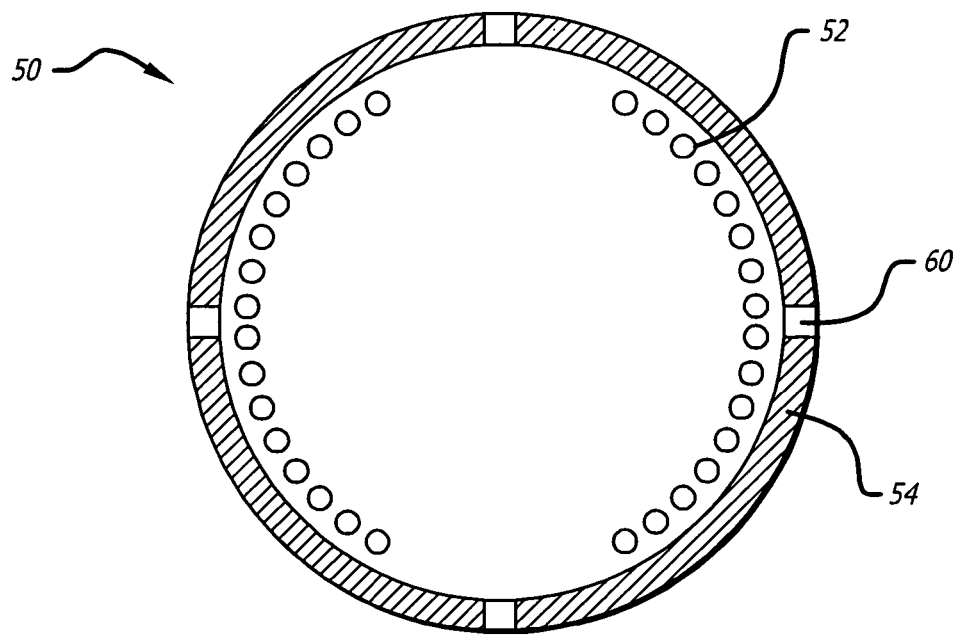
FIG. 3 is a cross-sectional view of the filter.

If the tip opening is larger than the inner diameter of the aspiration tube the aspiration system may include an in-line filter 50 as shown FIGS. 2 and 3. The in-line filter 50 may include a filter mesh 52 pressed into an outer case 54. The upstream tube 34U may be connected to the handpiece. The filter mesh 52 may have a U-shape to maximize the volume of the filter.

The aspiration system may include a downstream aspiration tube 34D attached to an integral luer 56 of the filter case 54. The downstream tube 34D may also be connected to the vacuum pump. The system may include an upstream aspiration tube 34U with a flared end 58 that can be pressed into the filter casing 54. The flared end, tubing and filter should be constructed so that there is not a flow restriction at the upstream portion of the filter. The casing 54 may have longitudinal grooves 60 as shown in FIG. 3 that allow small particle to escape the filter. For a 0.04 inch tubing the filter may have an aperture of approximately 0.01 inches.

The aspiration tube 34 provides for an aspiration system that can minimize vacuum surges without introducing complicated parts or increased costs to the system.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical aspiration system, comprising:
   a pump;
   a tube that is connected to said pump, said tube having an inner diameter less than 0.05 inches but no less than 0.01 inches, and a length of at least 3 feet, and
   a filter coupled to said tube, the filter including a filter mesh within a filter case, the filter case having an inner surface that includes a plurality of longitudinal grooves running along and outside of the filter mesh.

2. The aspiration system of claim 1, wherein said filter is in-line with said tube.

3. The aspiration system of claim 1, wherein said filter mesh has a U-shape.

4. The aspiration system of claim 1, wherein said tube creates a pressure drop of at least 150 mmHg and allows a maximum flow of 60 cc/min when said pump is generating a maximum vacuum.

5. The aspiration system of claim 1, wherein the filter case is cylindrical and the longitudinal grooves are disposed radially outside the filter mesh.

6. The aspiration system of claim 1, wherein the longitudinal grooves are configured to allow small particle to escape the filter.

7. A medical cutting system, comprising:
   a handpiece;
   a cutting element attached to said handpiece;
   a tube that is connected to said handpiece and that has an inner diameter less than 0.05 inches but no less than 0.01 inches, and a length of at least 3 feet;
   a pump connected to said tube; and
   a filter coupled to said tube, the filter including a filter mesh within a filter case, the filter case having an inner surface that includes a plurality of longitudinal grooves running along and outside of the filter mesh.

8. The cutting system of claim 7, wherein said filter is in-line with said tube.

9. The cutting system of claim 7, wherein said filter mesh has a U-shape.

10. The cutting system of claim 7, wherein said tube creates a pressure drop of at least 150 mmHg and allows a maximum flow of 60 cc/min when said pump is generating a maximum vacuum.

11. The cutting system of claim 7, wherein the filter case is cylindrical and the longitudinal grooves are disposed radially outside the filter mesh.

12. The cutting system of claim 7, wherein the longitudinal grooves are configured to allow small particle to escape the filter.

* * * * *